United States Patent
Hayag et al.

(10) Patent No.: US 9,662,277 B2
(45) Date of Patent: May 30, 2017

(54) ADHESIVE PREPARATION FOR MANDIBULAR PROSTHESES

(71) Applicant: TRIPP GMBH & CO. KG, Oppenau (DE)

(72) Inventors: Hans Hayag, Offenburg (DE); Lutz Henkel, Bad Bellingen / Hertingen (DE); Hanspeter Söllner-Tripp, Oberkirch (DE)

(73) Assignee: TRIPP GMBH & CO. KG, Oppenau (DE)

( * ) Notice: Subject to any disclaimer, the term of this patent is extended or adjusted under 35 U.S.C. 154(b) by 0 days.

(21) Appl. No.: 14/654,957

(22) PCT Filed: Jul. 4, 2013

(86) PCT No.: PCT/EP2013/002573
§ 371 (c)(1),
(2) Date: Jun. 23, 2015

(87) PCT Pub. No.: WO2014/106516
PCT Pub. Date: Jul. 10, 2014

(65) Prior Publication Data
US 2015/0313800 A1 Nov. 5, 2015

(30) Foreign Application Priority Data
Jan. 3, 2013 (WO) .................. PCT/EP2013/000007

(51) Int. Cl.
*A61K 6/083* (2006.01)
*A61K 6/097* (2006.01)
*A61K 6/00* (2006.01)

(52) U.S. Cl.
CPC .......... *A61K 6/0026* (2013.01); *A61K 6/0008* (2013.01); *A61K 6/0047* (2013.01); *A61K 6/0088* (2013.01); *A61K 6/083* (2013.01); *A61K 6/097* (2013.01)

(58) Field of Classification Search
None
See application file for complete search history.

(56) References Cited

U.S. PATENT DOCUMENTS

| | | | | |
|---|---|---|---|---|
| 3,003,988 A | * | 10/1961 | Germann | C08F 8/00 106/35 |
| 3,215,599 A | * | 11/1965 | Thau | A61K 9/0014 424/642 |
| 4,318,742 A | * | 3/1982 | Lokken | A61K 6/0026 106/162.8 |
| 4,373,036 A | * | 2/1983 | Chang | C09J 101/284 106/35 |

(Continued)

FOREIGN PATENT DOCUMENTS

| | | |
|---|---|---|
| DE | 10 2005 031 771 A1 | 1/2007 |
| WO | 00/18356 A1 | 4/2000 |

(Continued)

*Primary Examiner* — Peter A Salamon
(74) *Attorney, Agent, or Firm* — McGlew and Tuttle, P.C.

(57) ABSTRACT

A vegetable-based adhesive preparation for mandibular prostheses. The preparation has improved adhesive properties, consistency and stability as a result of a filler containing: 35 to 45 wt. % vegetable oil; 25 to 50 wt % structure-forming stabilizer; 5 to 15 wt % bonding agent; and silicon oxide making up the remainder.

17 Claims, 1 Drawing Sheet

(56) References Cited

U.S. PATENT DOCUMENTS

| | | | |
|---|---|---|---|
| 4,521,551 A * | 6/1985 | Chang | C08L 29/10 |
| | | | 106/35 |
| 4,542,168 A | 9/1985 | Chang et al. | |
| 4,569,955 A * | 2/1986 | Dhabhar | A61K 6/0026 |
| | | | 106/35 |
| 5,006,571 A * | 4/1991 | Kumar | C09J 101/286 |
| | | | 523/120 |
| 5,011,868 A | 4/1991 | Keegan | |
| 5,093,387 A * | 3/1992 | Schobel | A61K 6/0026 |
| | | | 424/49 |
| 5,561,177 A * | 10/1996 | Khaledi | A61K 6/0026 |
| | | | 433/180 |
| 6,110,989 A * | 8/2000 | Clarke | A61K 6/0026 |
| | | | 523/120 |
| 6,197,288 B1 * | 3/2001 | Mankoo | A23G 3/346 |
| | | | 424/439 |
| 6,475,498 B1 * | 11/2002 | Rajaiah | A61K 6/0026 |
| | | | 106/35 |
| 6,905,672 B2 * | 6/2005 | Rajaiah | A61K 6/0026 |
| | | | 424/49 |
| 2003/0007937 A1 * | 1/2003 | Lawlor | A23G 3/346 |
| | | | 424/57 |
| 2004/0241617 A1 | 12/2004 | Allred et al. | |
| 2005/0075497 A1 * | 4/2005 | Utz | A23L 1/0526 |
| | | | 536/114 |
| 2007/0037717 A1 | 2/2007 | Clark et al. | |
| 2009/0136893 A1 | 5/2009 | Zegarelli | |
| 2009/0239972 A1 * | 9/2009 | Rajaiah | A61K 6/0023 |
| | | | 523/120 |
| 2011/0293540 A1 * | 12/2011 | Musa | C08F 226/06 |
| | | | 424/49 |
| 2012/0296006 A1 * | 11/2012 | Bogaert | A61K 6/0026 |
| | | | 523/118 |
| 2013/0197124 A1 * | 8/2013 | Bogaert | A61K 6/0026 |
| | | | 523/105 |

FOREIGN PATENT DOCUMENTS

| | | |
|---|---|---|
| WO | 01/30303 A1 | 5/2001 |
| WO | 01/41710 A1 | 6/2001 |
| WO | 2007/056607 A2 | 5/2007 |
| WO | 2011/088988 A1 | 7/2011 |

* cited by examiner

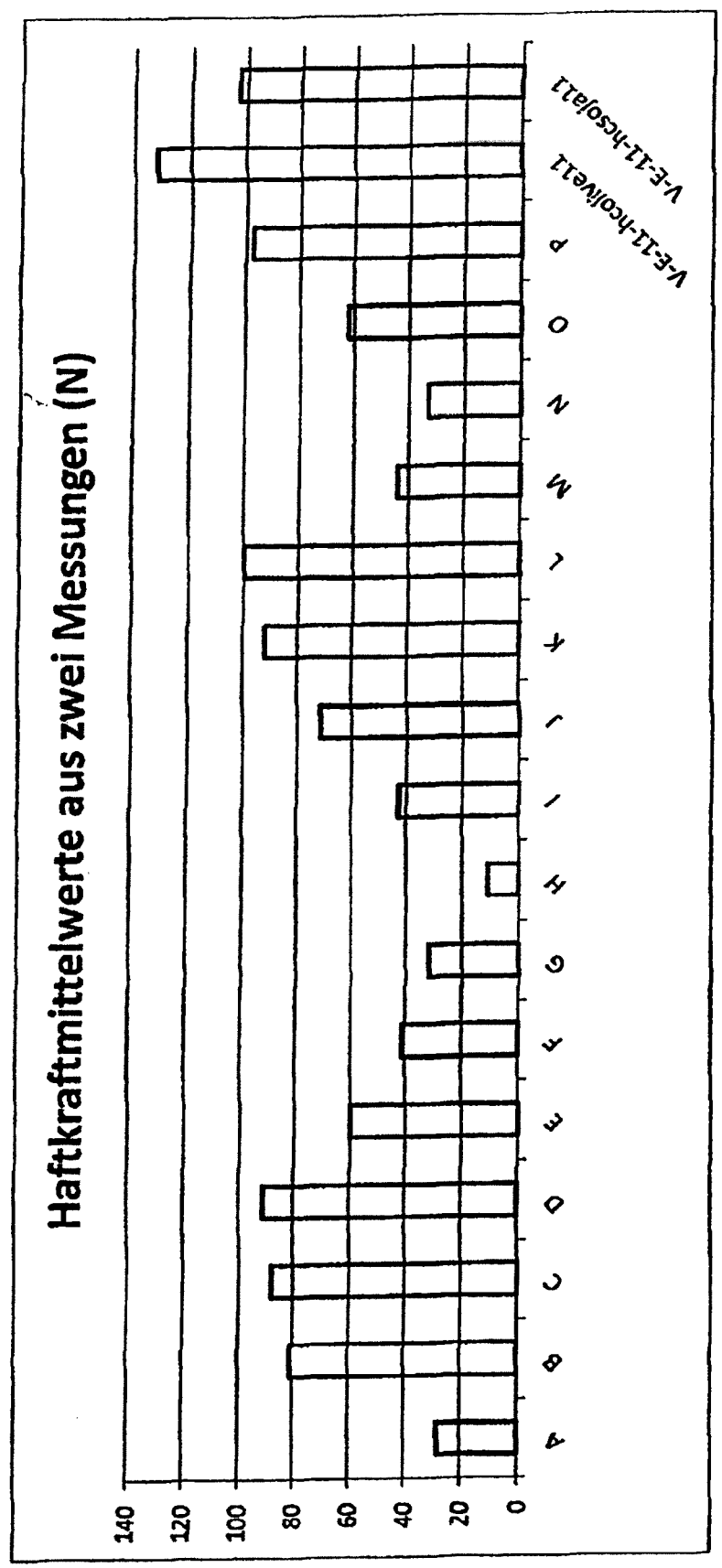

ADHESIVE PREPARATION FOR MANDIBULAR PROSTHESES

CROSS REFERENCE TO RELATED APPLICATIONS

This application is a United States National Phase application of International Application PCT/EP2013/002573 filed on Jul. 4, 2013 and claims the benefit of priority under 35 U.S.C. §119 of International Application PCT/EP2013/000007 filed Jan. 3, 2013, the entire contents of which are incorporated herein by reference.

FIELD OF THE INVENTION

The invention pertains to an adhesive preparation for mandibular prostheses.

BACKGROUND OF THE INVENTION

Such an adhesive preparation for mandibular prostheses is known from DE 10 2005 031 771. The adhesive preparation there contains viscous paraffin in a percentage of 25 wt. % to 35 wt. % and/or white vaseline in a percentage of 10 wt. % to 20 wt. % as the cream basis, a carbomer (polyacrylic acid) as a bonding agent with a percentage of 1 wt. % to 15 wt. % as well as one or at least two carboxymethylcellulose(s) or an alkali metal salt or alkaline earth metal salt of same as a bonding agent with a percentage of 15 wt. % to 50 wt. % as well as highly disperse silicic acid as a filler with 0.2 wt. % to 2.0 wt. %.

Commercially available adhesive creams use paraffin/vaseline to obtain a pliable preparation. In prosthesis wearers, irritations of parts of the pharynx may occur. The commercially available adhesive creams for prostheses also use for the most part the raw material Gantrez (calcium/sodium PVM/MA copolymer) from the firm of ISP, with regard to which is given the risk of possible raw material shortages, raw material dependencies and time delays of the raw material availability.

Therefore, it was already suggested in practice to use olive oil instead of paraffin or vaseline as the carrier substance. The prior-art adhesive cream has, however, only an adhesiveness in the lower acceptable range at best.

If one wants to replace paraffin or vaseline with a vegetable oil, then the remaining components of the starting adhesive preparation may not be retained as such. Because of the completely different consistency of olive oil compared to vaseline or paraffin, no acceptable adhesive preparation is then obtained.

In this case, the requirements on such an adhesive cream with regard to adhesiveness, consistency and stability must be taken into account.

SUMMARY OF THE INVENTION

A basic object of the present invention is to create an adhesive preparation for mandibular prostheses, which is nevertheless suitable as such while dispensing with paraffin and/or vaseline as the basic or cream substance and has especially not only good subjective, but also objective adhesive properties as well as, in addition, a homogeneous consistency and high stability over time.

According to the present invention the object mentioned is accomplished by an adhesive preparation for mandibular prostheses containing:

35 wt. % to 50 wt. % vegetable oil,
25 wt. % to 50 wt. % structure-forming stabilizer,
5 wt. % to 15 wt. % bonding agent, and
the remainder being a filler containing silicon oxide.

Preferably, the adhesive cream consists exclusively of these components. The sum of vegetable oil and stabilizer lie below 90 wt. % here.

The filler or its at least decisive main component silicon dioxide (silica) is highly porous, i.e., the filler and/or silicon dioxide has a density of 1.9 $g/cm^3$ to 2.1 $g/cm^3$. While silicon dioxide is usually prepared as fused or pyrogenic silicon dioxide, provisions are made in a preferred embodiment for the filler to contain silicon dioxide precipitated from a solution. According to another preferred embodiment, provisions are made for the particle size to lie in the range of 1 mm to 40 mm. Particle size here does not designate the primary particle size, which lies at 5-100 nm, but the size of the particles formed by agglomeration of the primary particles, or of the agglomerate particles or the size of the agglomerate. The average pore size is preferably >30 nm. While the surface of the particles preferably is in the range of 5 $m^2/g$ to 100 $m^2/g$, this value is most preferably <than 50 $m^2/g$.

As the replacement for paraffin/vaseline, vegetable oils guarantee the pliability of the preparation. With the use of vegetable oils, based on the chemical composition, an anti-inflammatory effect can be achieved in the event of corresponding irritations. The bonding agent contributes to the pliability as well. The filler brings about the necessary thickening and regulates the viscosity.

It was determined that besides olive oil, especially also Saint John's wort oil, almond oil, rapeseed oil, soybean oil, sunflower seed oil, grapeseed oil and/or wheat germ oil are also preferably possible as vegetable oil.

Carboxymethylcellulose (CMC), especially as sodium salt, but also as other alkali salt or alkaline earth salt of the said cellulose or hydroxyethylcellulose (HEC), especially Walocel, is preferably provided as a structure-forming stabilizer with the percentage mentioned. As an alternative, the adhesive preparation according to the present invention may also contain hydroxypropylcellulose (HPC) or xanthan gum as a structure-forming stabilizer.

The bonding agent in the adhesive preparation according to the present invention preferably contains polyacrylic acid with the above-mentioned weight percentage, whereby the bonding agent is preferably polyacrylic acid, and is especially the exclusive bonding agent. Thereby, the bonding agent with a dynamic viscosity equal to or greater than 30,000 mPas is preferably used. Carbomers especially represented by the trade names Carbopol 971P NF and Carbopol 974P NF are possible as concrete polyacrylic acid or carbomers. By means of this bonding agent, the bonding agent usually used in an adhesive composition (methyl vinyl ether), maleic acid anhydride (copolymer), which contains zinc, which is considered to be harmful, can be avoided.

Preferred embodiments of the present invention provide for the filler to be highly porous, for the filler to contain silicon dioxide precipitated from a solution, for the density of the filler, preferably at least of the silicon dioxide essentially constituting it, to be between 0.08 $g/cm^3$ and 0.23 $g/cm^3$, preferably between 0.19 $g/cm^3$ and 0.21 $g/cm^3$, and/or for the particle size to lie in the range of 1 mm to 40 mm, whereby the average pore size is preferably >30 nm.

While the filler may consist exclusively of silicon oxide (silica), in the preferred embodiment, it contains a low percentage of less than 0.1 wt. %, but preferably at least 0.001 wt. %, most preferably at least 0.01 wt. % styrene-isoprene copolymer and/or less than 0.1 wt. %, preferably at least 0.001 wt. %, most preferably at least 0.01 wt. % aluminum stearate.

While the compositions mentioned above guarantee suitable adhesive preparations for mandibular prostheses with the weight percentages given there, provisions are made in a preferred embodiment for 40 wt. % to 50 wt. % to make up the vegetable oil percentage, 40 wt. % to 50 wt. % to make up that of the structure-forming stabilizer, 8 wt. % to 13 wt. % to make up the bonding agent and/or 3 wt. % to 6 wt. % to make up the filler, whereby the sum of all components amounts to 100 wt. % in each case.

An adhesive preparation with a plastic, soft consistency, which is neither too stiff nor too flowable, is created by the present invention. The adhesive preparation has, moreover, a suitable adhesive force above a lower acceptable value of 40 N, without the risk of a too high adhesive force of over 150 N, especially over 180 N being given.

Moreover, the adhesive preparation according to the present invention has a high stability over time and does not decompose even in the event of a long storage time.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
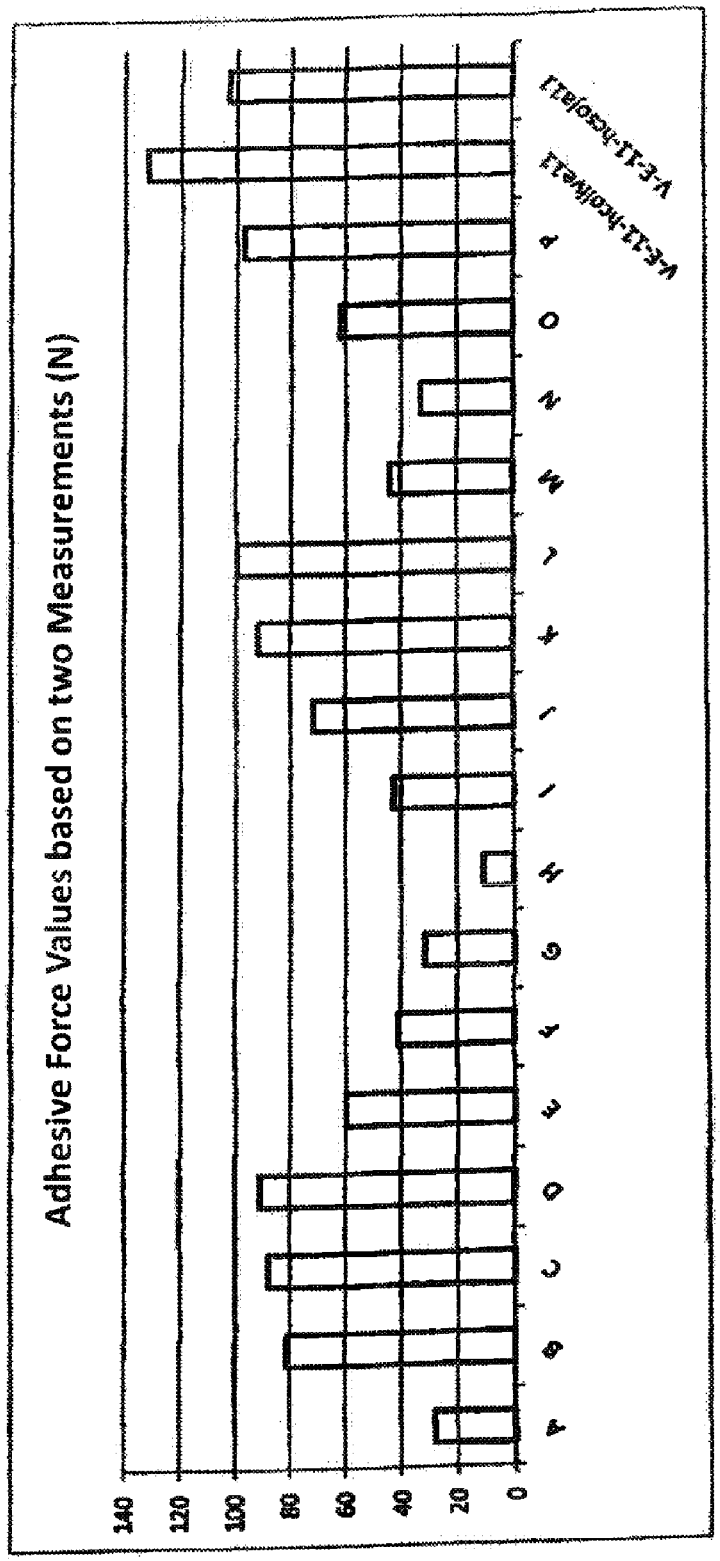
FIG. 1 is a graphic view showing adhesive force values for various adhesive preparations.

Referring to the drawings in particular, FIG. 1 shows adhesive force mean values from two measurements in Newtons (N) for a plurality of commercially available adhesive preparations, which are designated with A through P as well as two adhesive force preparations according to the present invention based on olive oil, on the one hand, and based on soybean oil, on the other hand, whose exact composition appears from Tables 1 through 3.

The adhesive composition H is the composition known from practice, which is based on olive oil and does not contain earth-oil-based basic substances, such as paraffin or vaseline, which are given I through P with all other adhesive compositions A through G.

It is shown that while the prior-art, olive-oil-based adhesive composition has a comparably extremely low adhesive force of less than 20 N with otherwise acceptable adhesive force values of over 40 N or 50 N, while the likewise vegetable-oil-based adhesive force compositions according to the present invention V-E-11-hcolive 11 and VE-E-11-hcsojall show optimal adhesive force values in the range of over 100 N, whereby, as stated, adhesive force values of over 50 N are still completely acceptable, which, however, are obtained up to now only by paraffin-based or vaseline-based adhesive force compositions.

The filler of the tables is continuously silicon-oxide-based filler with 99% silicon oxide (silica) and low percentages of styrene-isoprene copolymer and aluminum stearate of less than 0.1 wt. % each. If no specific data are contained in each of the tables, the component designations and percentages indicated in the heading of the tables apply. Deviating components are themselves optionally indicated in the individual fields of the table, just as deviating percentages of the components indicated in the heading.

The adhesive force and consistency measurements, which are the basis of the attached Tables 1 through 3 are carried out as follows, the latter analogous to DIN 10331/ISO 16305:

The adhesive force measurements are carried out with the structure measuring apparatus A-XT plus from Stable Micro Systems Ltd., Godalming, Surrey, Great Britain. For the measurement, 0.75 g (±0.01 g) of adhesive cream with a sample temperature of 25° C.±1° C. was applied to an unengraved side of the sample holder in lumps. The forward and testing speeds are each 0.5 mm/sec, the return speed is 10.0 mm/sec. The pressing pressure was 1,000.0 g, and the trigger value was 5.0 g. Five hundred measurement points were determined per measurement.

The consistency measurement was carried out such that 1.0 g of the test substance tempered to 20° C. is applied in lumps to a glass plate in the middle. The glass plate with the test substance was placed on the extensometer, tempered to 20° C., for 10 min. to 15 min., before another glass plate (diameter=11.5 cm) with a weight of 47.85 g was placed on. Then, the upper glass plate was weighted down with the test weight of the apparatus of 331.3 g (total weight 379.15 g). The diameter of the circle or ellipse formed was determined after 15 min.

An extremely preferred formulation V-E-11-hcsoja-11 according to the present invention containing 42 wt. % soybean oil, 9 wt. % polyacrylic acid as bonding agent, as is represented by the designation Carbopol 971P NF from the Lubrizol Corporation, Wickliffe, Ohio, USA, 44 wt. % of carboxymethylcellulose sold, for example, by the Dow Deutschland Anlagengesellschaft mbH, Schwalbach under the designation WALOCEL as structure-forming stabilizer and 5 wt. % filler is shown in line 1 in Table 1. This adhesive preparation has an optimal-soft-consistency of 4.4 cm to 4.5 cm with an adhesive force of 92 N, as FIG. 1 shows.

While the formulations 4 through 6 of Table 1 with consistencies between 3.5 cm and 3.8 cm have a likewise acceptable adhesive force of 63 N to 76 N, it is shown that the consistency of the adhesive preparation is too stiff or too firm (formulation 2 of Table 1) in the event of a sharper reduction of the vegetable oil percentage with simultaneous increasing of the carboxymethylcellulose percentage to markedly above 50%, and this may also not be compensated by reducing the filler (formulation 3 of Table 1).

Table 2 shows that the structure-forming stabilizer carboxymethylcellulose (Walocel) may basically also be completely—or even partially—substituted by the structure-forming stabilizer xanthan gum, whereby the adhesive force decreases slightly compared to carboxymethylcellulose, but absolutely also lies markedly above the lower limit of 40 N. Therefore, the table shows also that bonding agents with a markedly higher viscosity than 29,000 mPa may be used and absolutely very good adhesive values with suitable consistency are obtained.

Adhesive preparations according to the present invention have a body-compatible, particularly also mucous-membrane-compatible slightly acidic pH value of more than 5.

Surprisingly, formulations 4 and 5 of Table 3 show that the use of a suitable bonding agent—as used in the other compositions—a means suitable as a structure-forming stabilizer, such as Keldent, leads to a dramatic drop in the adhesive force, aside from the fact that the adhesive preparation is, moreover, also too stiff.

TABLE 1

ADHESIVE CREAM TEST SERIES 2011

| | | Natural Oil | | Carbopol 971P NF | | CMC | | Filler | | |
|---|---|---|---|---|---|---|---|---|---|---|
| | | 30% | 45% | 5% | 15% | 30% | 50% | 3% | 6% | PHYSICAL PROPERTIES |
| 1 | FORMULATION V-E-11-hcsoja-11 | | 42% | 9% | | | 44% | | 5% | Consistency = 4.4/4.5 cm Adhesive force = 92 N |
| 2 | V-E-11-hcsoja-12-a | x | | 9% | | | 56% | | 5% | => too firm, pliability absent! |
| 3 | V-E-11-hcsoja-12 | x | | 9% | | | 58% | x | | => too firm, pliability absent! |
| 4 | V-E-11-hcsoja-13 | | x | 9% | | | 40% | | x | Consistency = 3.8/3.8 cm Adhesive force = 76 N |
| 5 | V-E-11-hcsoja-14 | | x | x | | | 44% | | x | Consistency = 3.5/3.6 cm Adhesive force = 63 N |
| 6 | V-E-11-hcsoja-15 | | x | | x | 34% | | | x | Consistency = 3.5/3.5 cm Adhesive force = 75 N |

TABLE 2

ADHESIVE CREAM TEST SERIES 2011

| | | Natural Oil | | Carbopol 974P NF | | Structure | | Filler | | |
|---|---|---|---|---|---|---|---|---|---|---|
| | | 30% | 45% | 5% | 15% | 25% | 45% | 3% | 6% | PHYSICAL PROPERTIES |
| 1 | FORMULATION V-E-11-hcsoja-11 | | 42% | 9% Carbopol 971P NF | | | 44% Walocel 60,000 | | 5% | Consistency = 4.4/4.5 cm Adhesive force = 92 N |
| 2 | V-E-11-hccarb974-2 | | 45% | | 15% | | 35% Walocel 60,000 | | 5% | Consistency = 3.6/3.6 cm Adhesive force = 78 N |
| 3 | V-E-11-hccarb974-3 | | 45% | | 12% | | 38% Keldent | | 5% | Consistency = cm Adhesive force = 77 N |
| 4 | V-E-11-hccarb974-4 | | 42% | 9% | | | 44% Keldent | | 5% | Consistency = 3.6/3.6 cm Adhesive force = 69 N |

TABLE 3

ADHESIVE CREAM TEST SERIES 2011

| | | Natural Oil* | | Carbopol 971P NF** | | CMC (or) HEC (or) Xanthan Gum*** | | 99% Silica**** <0.1% styrene/isoprene copolymer <0.1% aluminum stearates | | |
|---|---|---|---|---|---|---|---|---|---|---|
| | | 30% | 45% | 5% | 15% | 25% | 45% | 3% | 6% | PHYSICAL PROPERTIES |
| 1 | PATENT FORMULATION V-E-11-hcsoja-11 | | 42% | 9% | | | 44% Walocel 60,000 | | 5% | Consistency = 4.4/4.5 cm Adhesive force = 92 N |
| 2 | V-E-11-hckel-1 | | 42% | 9% | | | 44% Keldent | | 5% | Consistency = 4.0/4.0 cm Adhesive force = 72 N |
| 3 | V-E-11-hckel-2 | | 42% | 9% | | | 44% Keltrol CG | | 5% | Consistency = 2.9/3.0 cm Adhesive force = 25 N |
| 4 | V-E-11-hckel-3 | | 42% | — | | | 53% Keldent | | 5% | Adhesive force = 1.3 N => too firm, pliability absent! |
| 5 | V-E-11-hckel-4 | | 42% | 9% Keldent | | | 44% Walocel 60,000 | | 5% | Adhesive force = 0.6 N => too firm, pliability absent! |
| 6 | V-E-11-hcnat-1 | | 42% | 9% | | | 44% Natrosol HX | | 5% | Adhesive force = 39 N => too firm, gritty, pliability absent! |

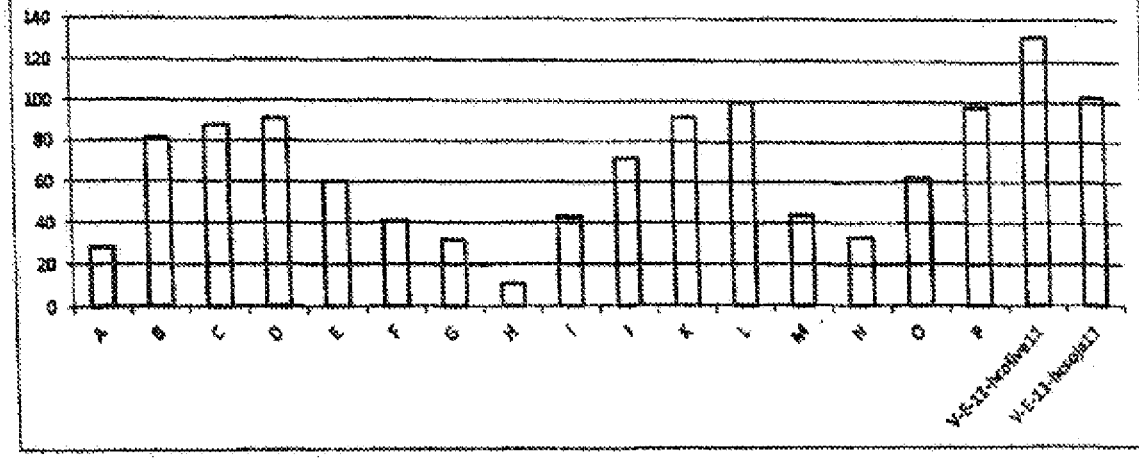

The invention claimed is:

1. Adhesive preparation for mandibular prostheses, comprising:
    35 wt. % to 50 wt. % vegetable oil;
    25 wt. % to 50 wt. % structure-forming stabilizer, the structure-forming stabilizer comprising one or more of xanthan gum, hydroxypropylcellulose (HPC) and carboxymethylcellulose (CMC), especially as carboxymethylcellulose sodium salt;
    5 wt. % to at most 9 wt. % polyacrylic acid as bonding agent; and
    a remainder, said remainder being 3 wt. % to 6 wt. % filler containing silicon oxide and having a density between 0.08 g/cm$^3$ and 0.23 g/cm$^3$, a particle size in a range of 1 to 40 mm, said adhesive preparation comprising an adhesive force between 40 N and 150 N.

2. Adhesive preparation in accordance with claim 1, wherein the vegetable oil is one or more of Saint John's wort oil, almond oil, olive oil, rapeseed oil, soybean oil, sunflower seed oil, grapeseed oil, and wheat germ oil.

3. Adhesive preparation in accordance with claim 1, wherein the filler contains silicon dioxide precipitated from a solution.

4. Adhesive preparation in accordance with claim 1, wherein a density of the filler, preferably at least of the silicon dioxide is between 0.19 g/cm$^3$ and 0.21 g/cm$^3$.

5. Adhesive preparation in accordance with claim 1, wherein an average pore size of the adhesive preparation is greater than 30 nm.

6. Adhesive preparation in accordance with claim 1, wherein the filler contains less than 0.1 wt. % styrene-isoprene copolymer in relation to the weight of the filler.

7. Adhesive preparation in accordance with claim 1, wherein the filler contains less than 0.1 wt. % aluminum stearate in relation to the weight of the filler.

8. Adhesive preparation in accordance with claim 1, wherein said adhesive preparation comprises between 70 N and 110 N.

9. Adhesive preparation in accordance with claim 1, wherein a vegetable oil percentage of 40 wt. % to 45 wt. % is provided.

10. Adhesive preparation in accordance with claim 1, wherein 40 wt. % to 50 wt. % structure-forming stabilizer is provided.

11. Adhesive preparation in accordance with claim 1, wherein 40 wt. % to 45 wt. % vegetable oil, 41 wt. % to 46 wt. % structure-forming stabilizer, and 4 wt. % to 6 wt. % filler containing silicon oxide are provided.

12. Adhesive preparation in accordance with claim 1, wherein the filler contains at least 0.001 wt. % styrene-isoprene copolymer in relation to the weight of the filler.

13. Adhesive preparation in accordance with claim 1, wherein the filler contains at least 0.01 wt. % styrene-isoprene copolymer in relation to the weight of the filler.

14. Adhesive preparation in accordance with claim 1, wherein the filler contains at least 0.001 wt. % aluminum stearate in relation to the weight of the filler.

15. Adhesive preparation in accordance with claim 1, wherein the filler contains at least 0.01 wt. % aluminum stearate in relation to the weight of the filler.

16. Adhesive preparation for mandibular prostheses, comprising:
    an adhesive preparation composition consisting essentially of 35 wt. % to 50 wt. % vegetable oil, 25 wt. % to 50 wt. % structure-forming stabilizer, 5 wt. % to at most 9 wt. % polyacrylic acid as bonding agent and a remainder, said remainder being 3 wt. % to 6 wt. % filler containing silicon oxide, the structure-forming stabilizer being one or more of xanthan gum, hydroxypropylcellulose (HPC), carboxymethylcellulose sodium salt and carboxymethylcellulose (CMC).

17. Adhesive preparation for mandibular prostheses, comprising:
    an adhesive preparation composition consisting of 35 wt. % to 50 wt. % vegetable oil, 25 wt. % to 50 wt. % structure-forming stabilizer, 5 wt. % to at most 9 wt. % polyacrylic acid as bonding agent and a remainder, said remainder being 3 wt. % to 6 wt. % filler containing silicon oxide, the structure-forming stabilizer being one or more of xanthan gum, hydroxypropylcellulose (HPC), carboxymethylcellulose sodium salt and carboxymethylcellulose (CMC).

* * * * *

UNITED STATES PATENT AND TRADEMARK OFFICE
CERTIFICATE OF CORRECTION

PATENT NO. : 9,662,277 B2  
APPLICATION NO. : 14/654957  
DATED : May 30, 2017  
INVENTOR(S) : Hans Hayag, Lutz Henkel and Hanspeter Söllner-Tripp Page 1 of 3

It is certified that error appears in the above-identified patent and that said Letters Patent is hereby corrected as shown below:

On the Title Page

Replace title page with attached title page.

In the Drawings

Replace drawing sheet 1 of 1, with attached drawing sheet 1 of 1.

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*

(12) United States Patent
Hayag et al.

(10) Patent No.: US 9,662,277 B2
(45) Date of Patent: May 30, 2017

(54) ADHESIVE PREPARATION FOR MANDIBULAR PROSTHESES

(71) Applicant: TRIPP GMBH & CO. KG, Oppenau (DE)

(72) Inventors: Hans Hayag, Offenburg (DE); Lutz Henkel, Bad Bellingen / Hertingen (DE); Hanspeter Söllner-Tripp, Oberkirch (DE)

(73) Assignee: TRIPP GMBH & CO. KG, Oppenau (DE)

(*) Notice: Subject to any disclaimer, the term of this patent is extended or adjusted under 35 U.S.C. 154(b) by 0 days.

(21) Appl. No.: 14/654,957

(22) PCT Filed: Jul. 4, 2013

(86) PCT No.: PCT/EP2013/002573
§ 371 (c)(1),
(2) Date: Jun. 23, 2015

(87) PCT Pub. No.: WO2014/106516
PCT Pub. Date: Jul. 10, 2014

(65) Prior Publication Data
US 2015/0313800 A1 Nov. 5, 2015

(30) Foreign Application Priority Data
Jan. 3, 2013 (WO) ................ PCT/EP2013/000007

(51) Int. Cl.
*A61K 6/083* (2006.01)
*A61K 6/097* (2006.01)
*A61K 6/00* (2006.01)

(52) U.S. Cl.
CPC .......... *A61K 6/0026* (2013.01); *A61K 6/0008* (2013.01); *A61K 6/0047* (2013.01); *A61K 6/0088* (2013.01); *A61K 6/083* (2013.01); *A61K 6/097* (2013.01)

(58) Field of Classification Search
None
See application file for complete search history.

(56) References Cited

U.S. PATENT DOCUMENTS

| 3,003,988 | A | * | 10/1961 | Germann | C08F 8/00 106/35 |
| 3,215,599 | A | * | 11/1965 | Thau | A61K 9/0014 424/642 |
| 4,318,742 | A | * | 3/1982 | Lokken | A61K 6/0026 106/162.8 |
| 4,373,036 | A | * | 2/1983 | Chang | C09J 101/284 106/35 |

(Continued)

FOREIGN PATENT DOCUMENTS

| DE | 10 2005 031 771 A1 | 1/2007 |
| WO | 00/18356 A1 | 4/2000 |

(Continued)

*Primary Examiner* — Peter A Salamon
(74) *Attorney, Agent, or Firm* — McGlew and Tuttle, P.C.

(57) ABSTRACT

A vegetable-based adhesive preparation for mandibular prostheses. The preparation has improved adhesive properties, consistency and stability as a result of a filler containing: 35 to 45 wt. % vegetable oil; 25 to 50 wt % structure-forming stabilizer; 5 to 15 wt % bonding agent; and silicon oxide making up the remainder.

17 Claims, 1 Drawing Sheet